United States Patent
Kassatly et al.

(10) Patent No.: US 8,215,302 B2
(45) Date of Patent: Jul. 10, 2012

(54) DISCONTINUOUS POSITIVE AIRWAY PRESSURE DEVICE AND METHOD OF REDUCING SLEEP DISORDERED BREATHING EVENTS

(76) Inventors: L. Samuel A Kassatly, San Jose, CA (US); Michelle M Kassatly, San Jose, CA (US); Danielle M Kassatly, San Jose, CA (US); Gabrielle M Kassatly, San Jose, CA (US)

( * ) Notice: Subject to any disclaimer, the term of this patent is extended or adjusted under 35 U.S.C. 154(b) by 457 days.

(21) Appl. No.: 12/564,561

(22) Filed: Sep. 22, 2009

(65) Prior Publication Data
US 2011/0071444 A1   Mar. 24, 2011

(51) Int. Cl.
*A61M 16/00* (2006.01)
*A62B 7/00* (2006.01)

(52) U.S. Cl. ......... 128/204.23; 128/200.24; 128/204.18; 128/204.21; 128/204.26

(58) Field of Classification Search ............. 128/200.24, 128/200.26, 207.14, 207.16, 207.18, 206.21, 128/206.29, 207.13, 206.11, 857, 859–861; 600/529, 532
See application file for complete search history.

(56) References Cited

U.S. PATENT DOCUMENTS

| | | | |
|---|---|---|---|
| 3,730,179 A * | 5/1973 | Williams | 128/204.18 |
| 4,655,213 A | 4/1987 | Rapoport et al. | |
| 5,238,006 A | 8/1993 | Markowitz | |
| 5,433,193 A | 7/1995 | Sanders et al. | |
| 5,954,050 A * | 9/1999 | Christopher | 128/204.23 |
| 7,353,826 B2 | 4/2008 | Sleeper et al. | |
| 7,481,224 B2 | 1/2009 | Nelson et al. | |
| 7,487,777 B2 | 2/2009 | Gunaratnam et al. | |
| 7,487,778 B2 * | 2/2009 | Freitag | 128/207.14 |
| D589,140 S | 3/2009 | Guney et al. | |
| 7,533,670 B1 * | 5/2009 | Freitag et al. | 128/204.23 |
| 7,578,013 B2 | 8/2009 | Aikman | |
| 7,578,294 B2 | 8/2009 | Pierro et al. | |
| 7,581,542 B2 | 9/2009 | Abramson | |

OTHER PUBLICATIONS

R. Pierce, et al., "Upper Airway Collapsibility, Dilator Muscle Activation and Resistance in Sleep Apnoea," European Respiratory Journal, vol. 30, No. 2, pp. 345-353 (2007).
Isom S., et al., "Anatomy of Pharynx in Patients with Obstructive Sleep Apnea and in Normal Subjects," J Appl. Physiol. 1997: 82:1319-1326.
Shellock F. G., et al., "Occlusion and Narrowing of the Pharyngeal Airway in Obstructive Sleep Apnea: Evaluation by Ultrafast Spoiled GRASS MR Imaging," Am J of Roentgenology 1992:158:1019-1024.

* cited by examiner

Primary Examiner — Annette Dixon
(74) Attorney, Agent, or Firm — Samuel A Kassatly

(57) ABSTRACT

A Discontinuous Positive Airway Pressure (DPAP) device and method of using the same for reducing sleep disordered breathing events, such as sleep apnea and snoring. The DPAP device provides selective excitation to the pharyngeal conduit or another muscle or cartilage along the respiratory path, a predetermined period of time before the end of the expiration stage, in order to prematurely reverse the respiratory cycle before the total collapse of the pharyngeal conduit, thus enabling the inhalation stage to reopen and refill the pharyngeal conduit.

20 Claims, 4 Drawing Sheets

DISCONTINUOUS POSITIVE AIRWAY PRESSURE DEVICE AND METHOD OF REDUCING SLEEP DISORDERED BREATHING EVENTS

FIELD OF THE INVENTION

The present invention relates in general to the field of sleep disorders, and in particular to a device, system, and method for reducing sleep disordered breathing events, such as sleep apnea and snoring.

BACKGROUND OF THE INVENTION

Sleep apnea is a breathing disorder characterized by brief disruptions of breathing during sleep. When a person stops breathing during sleep due to sleep apnea, the balance of oxygen and carbon dioxide in the blood is upset. This imbalance stimulates the brain to restart the breathing process. The brain signals the person to wake up so that the muscles of the tongue and throat can increase the size of the airway, by allowing carbon dioxide to escape and oxygen to enter the airway. These waking episodes are necessary to restart breathing, disrupt sleep, and may cause daytime exhaustion.

There are two types of sleep apnea: central and obstructive. Obstructive Sleep Apnea (OSA) and Central Sleep Apnea (CSA). OSA is the most common type of sleep apnea. It is caused by a breathing obstruction, which stops the airflow in the nose and mouth. CSA is less common than OSA, and is manifested as a central nervous system disorder that occurs when the brain signal telling the body to breathe is delayed. CSA can be caused by disease or injury involving the brainstem, such as a stroke, a brain tumor, a viral brain infection, or a chronic respiratory disease.

While the causes of apnea are different in CSA and OSA, the symptoms and results are generally similar, namely a deprivation of oxygen and poor sleep. The treatments for CSA include medications that stimulate the need to breathe and administration of oxygen. As used herein, sleep apnea includes either CSA or OSA.

Normally, the muscles of the upper part of the throat keep the airway open to permit airflow into the lungs. When the muscles of the upper airway relax and sag, the relaxed tissues may vibrate as air flows past the tissues during breathing, resulting in snoring.

When a person has OSA, the throat collapses during sleep, blocking the airway and preventing air from getting to the lungs. Generally, the throat muscles keep the throat and airway open. The resulting effect of OSA could become serious.

Exemplary sleep apneas treatment devices are described in the following publications: U.S. Pat. Nos. 4,655,213; 5,176,618; 5,238,006; 5,466,193; 7,353,826; 7,481,224; 7,487,777; 7,578,013; 7,578,294; 7,581,542; and D589140. Although several treatment devices have been described, the most common devices are classified into three categories: CPAP; dental appliances, oral devices, and lower jaw adjustment devices; and surgery.

CPAP (Continuous Positive Airway Pressure) is widely recommended for moderate to severe obstructive sleep apnea. CPAP entails wearing a mask-like device (or nose pillows) during sleep, in order to provide continuous, positive, pressurized air to prevent the airway from collapsing. While CPAP has proven to be effective for numerous patients, many people find the apparatus uncomfortable and awkward to use, particularly due to air leaks at higher pressures. Some improvements to the CPAP technology include options such as: "bilevel PAP," which switches from higher to lower air pressure during the expiration; and "AutoPAP", which uses an internal regulator that adjusts pressure rather than remaining at one fixed setting. Nonetheless, CPAP, as its name indicates, still uses "continuous" positive pressure.

Dental appliances, oral devices, and lower jaw adjustment devices may be made of acrylic and fit inside the mouth. Two oral devices that are commonly used are the mandibular repositioning device and the tongue retaining device. These oral devices open the airway by bringing the lower jaw or tongue forward during sleep. While oral devices are more convenient to use than CPAP, they are generally more effective for mild to moderate sleep apnea cases. A number of side effects may result from the use of the dental appliances, such as soreness, and damage to, or permanent change in position of the jaw, teeth, and mouth; saliva build-up; and nausea.

Surgery can increase the size of the patient's airway. The surgeon may remove tonsils, adenoids, or excess tissue at the back of the throat or inside the nose. The surgeon may reconstruct the jaw to enlarge the upper airway. Surgery may be an effective option for some patients; however, surgery carries the risks of surgical complications and infections.

While the foregoing treatment devices are useful for their intended purposes, there remains an unsatisfied need for a simple, cost-effective device, system, and method for reducing sleep disordered breathing events.

SUMMARY OF THE INVENTION

The present invention satisfies this need, and presents a device, system, and method for reducing sleep disordered breathing events (collectively referred to herein as "DPAP device", "the present DPAP device", or "Discontinuous Positive Airway Pressure Device").

The present DPAP device provides selective excitation to the pharyngeal conduit or another muscle or cartilage along the respiratory path, a predetermined period of time before the end of the expiration stage, in order to prematurely reverse the respiratory cycle before the total collapse of the pharyngeal conduit, thus enabling the inhalation stage to reopen and refill the pharyngeal conduit.

According to other embodiments of the present invention, the excitation source includes a puff of positive air pressure, oxygen, another gas, electrical, and/or an audible (or sound) vibratory wave.

According to still other embodiments, the excitation source is applied to pharyngeal conduit, the tongue, the palate, the epiglottis, salivary glands, and/or other muscles or cartilages that can cause the premature reversal of the respiratory cycle.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

FIGS. 3 and 4 are flow charts illustrating the process of using the DPAP device of FIG. 1 for reducing sleep disordered breathing events, as shown in the chart of FIG. 2, wherein FIG. 3 illustrates the general steps of a method for initializing the DPAP device of FIGS. 1 and 2, and further wherein FIG. 4 illustrates the general steps of a method using the DPAP device of FIGS. 1 and 2.

It should be understood that the sizes of the chart and the different components in the figures might not be in exact proportion, and are shown for visual clarity and for the purpose of explanation.

DETAILED DESCRIPTION OF PREFERRED EMBODIMENTS

Figure 1:
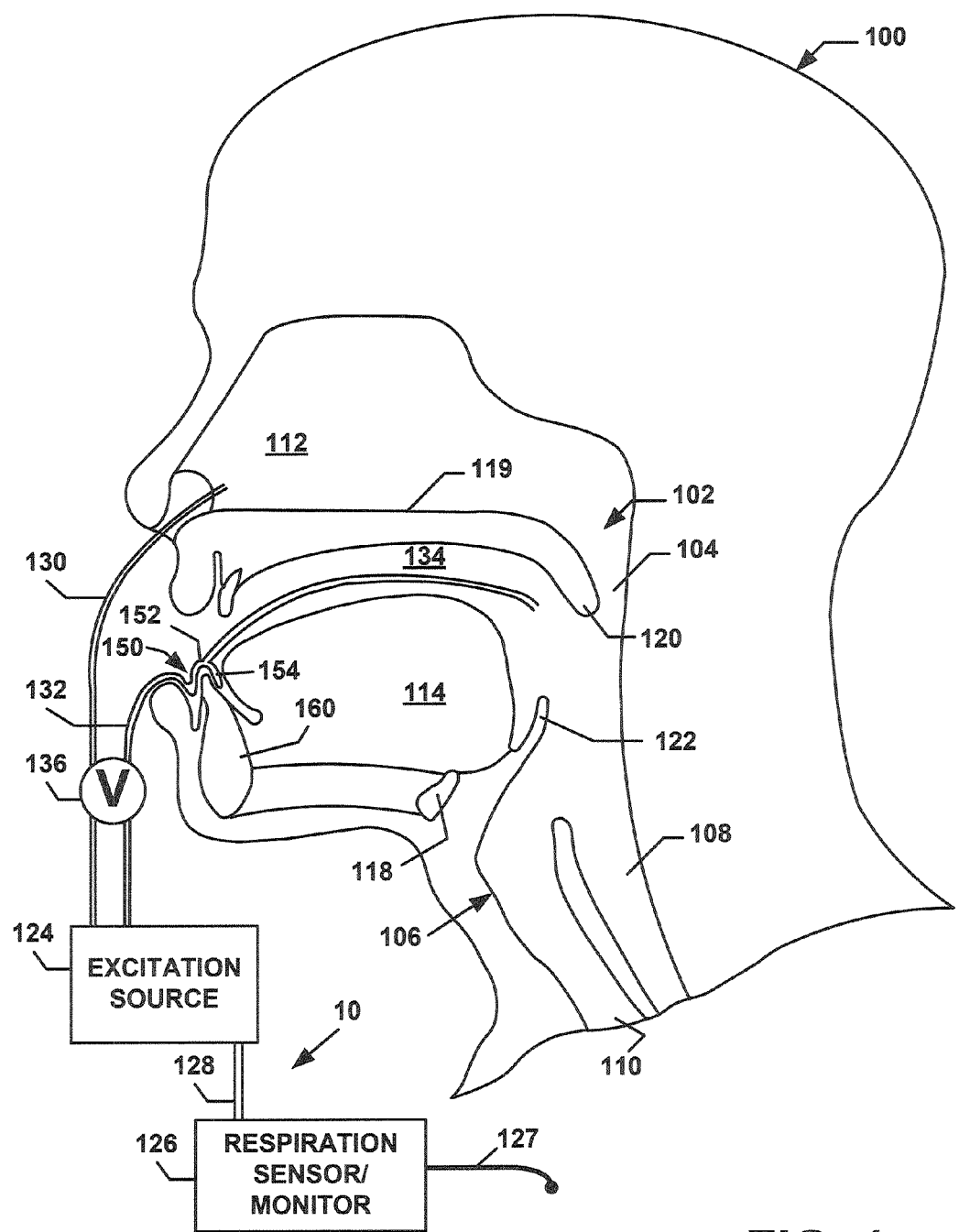
FIG. 1 is a side, cross-sectional, elevational view of a person's head showing the placement of the DPAP device according to the present invention.

FIG. 1 is a side view of a person's head 100 showing the placement of a DPAP device 10 according to the present invention. The person's upper airway 102 includes the pharynx 104 that splits into the larynx/trachea 106 and the esophagus 108. Although the tissue along this airway is responsive to the respiratory cycle, only the pharyngeal conduit 110, that includes the tissues in the region of the upper airway 102 that starts behind the nasal cavity 112 and ends in its connections to the larynx 106, is totally collapsible.

The pharyngeal structure and individual anatomic components within the upper airway 102 include the pharyngeal walls; the base of the tongue 114; the vallecula (or epiglottic vallecula); the hyoid bone 118 and its attachments; the soft palate 119 with uvula 120, the palatine tonsils with associated pillar tissue; and the epiglottis 122.

Figure 2:
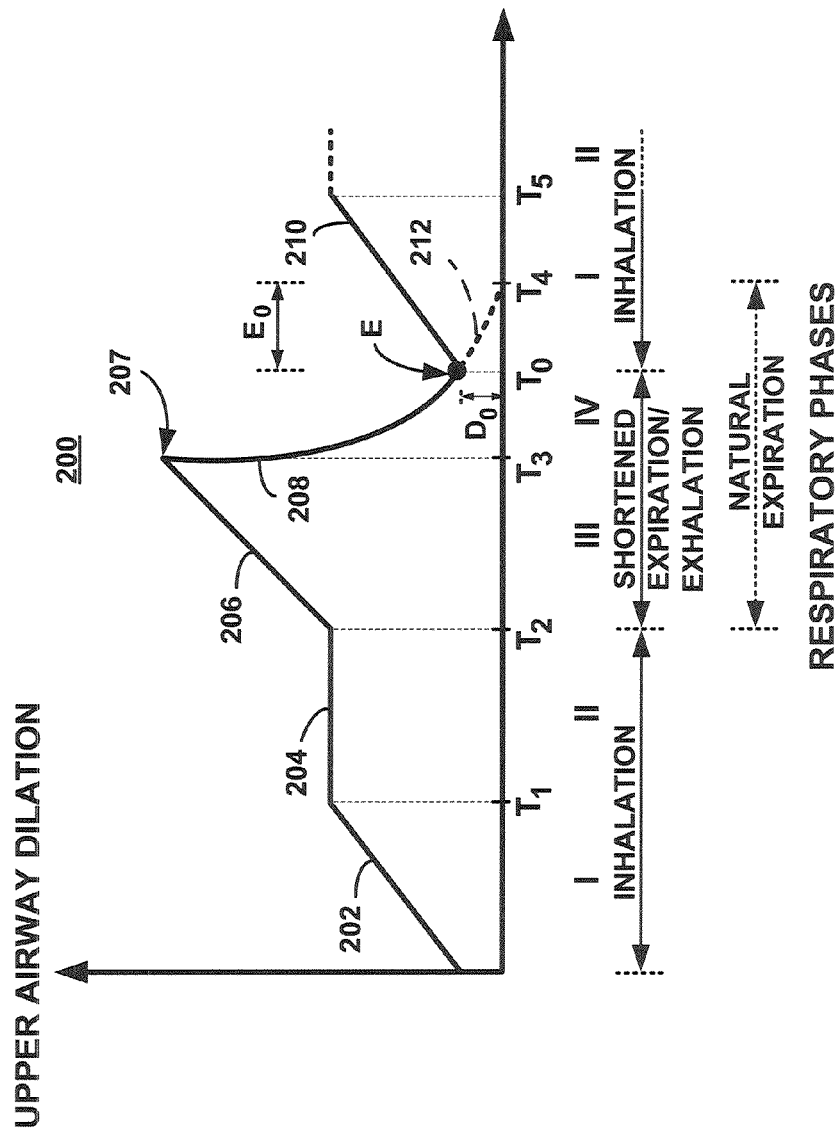
FIG. 2 is a chart illustrating the respiratory cycle using the DPAP device of FIG. 1.

FIG. 2 is a chart that illustrates an exemplary respiratory cycle 200 using the DPAP device 10 of FIG. 1 according to the present invention. This chart illustrates the variation (or dilation) of the cross-sectional area of the upper airway 102, with respect to the various phases of the respiratory cycle 200. At the initiation of inspiration (Phase I), and as illustrated by the segment 202, that ends at $T_1$, the upper airway 102 begins to dilate. Thereafter, and as illustrated by the segment 204, that ends at $T_2$, the upper airway 102 remains relatively constant through the remainder of inspiration (Phase II).

At the onset of expiration (Phase III), and as illustrated by the segment 206, that ends at $T_3$, the upper airway 102 begins to enlarge or dilate, reaching a maximum diameter at point 207. The upper airway 102 then starts to diminish in size, as illustrated by the segment 208, so that at the end of the natural expiration, without the corrective excitation of the present invention), it is at its narrowest, corresponding to the time $T_4$ when the upper airway (102) dilator muscles are least active, and positive intraluminal pressure is lowest.

The pharyngeal conduit 110 has the greatest potential for collapse and closure at the end of the expiration stage (at time $T_4$). The dilator muscle activation is directly related to airway narrowing and reduces resistance across patients with obstructive sleep apnea. R. Pierce, et al., "Upper Airway Collapsibility, Dilator Muscle Activation And Resistance In Sleep Apnoea," European Respiratory Journal, Volume 30, Number 2, pages 345-353 (2007).

Sleep is characterized by a reduction in upper airway dilator muscle activity. For the person with obstructive sleep apnea (OSA), it is believed that this change in muscle function causes pharyngeal narrowing and collapse. Current studies seem to support that OSA patients have an intrinsically structurally narrowed and more collapsible pharynx. Isono S., et al., "Anatomy of Pharynx in Patients with Obstructive Sleep Apnea and in Normal Subjects," J. Appl. Physiol. 1997: 82:1319-1326.

Although anatomic closure is often accentuated at specific sites, such as the velopharyngeal level, studies of closing pressures show that the narrowing and collapse usually occurs along the entire length of the pharynx 104. Shellock F. G., et al., "Occlusion and Narrowing of the Pharyngeal Airway in Obstructive Sleep Apnea: Evaluation by Ultrafast Spoiled GRASS MR Imaging," Am J of Roentgenology 1992:158:1019-1024.

The DPAP device 10 reduces sleep disordered breathing events by selectively providing excitation to the pharyngeal conduit 110 or another muscle, cartilage, or element along the respiratory path of the upper airway 102 (collectively referred to herein as "selective elements of the pharyngeal conduit"). This excitation is introduced at an optimal excitation point, E, at time $T_0$, which is selected at a predetermined, but short, excitation period of time $E_0$, before the virtual end, $T_4$, of the natural expiration stage. $T_0$-$T_4$ [$T_4$] is also referred to herein as "the virtual period".

The application of the excitation can also be quantified as a measure of the dilation of the pharyngeal conduit 110. In a preferred embodiment, the excitation is application as the dilation of the pharyngeal conduit 110 reaches approximately $D_0$. As a result, the excitation point E could be determined as a function of two parameters, the dilation $D_0$ and the excitation period $E_0$: $E(D_0, E_0)$.

These two parameters ($D_0$, $E_0$) vary for each individual, and are thus personalized. The selection of the excitation point E enables the premature reversal of the respiratory cycle before the total collapse of the pharyngeal conduit 110, and shortens the natural occurrence of the expiration or exhalation stage. As a result of such reversal, the inhalation stage is prematurely introduced, at about substantially the optimal excitation period $E_0$ prior to its natural initiation. The premature initiation of the inhalation phase (Phase I) prematurely reopens and commences the inflation of the pharyngeal conduit 110, prior to the expected total or substantial collapse of the pharyngeal conduit 110. The premature inflation of the pharyngeal conduit 110 prevents the occurrence of the apnic events.

More specifically, and still with reference to FIG. 2, the expiration stage is cut off at time $T_0$. Rather than allowing the pharyngeal conduit 110 to follow its natural course and dilate, or more accurately deflate, following the path 212 (shown in dotted lines), the pharyngeal conduit 110 is forced to be inflated along the path 210 (that ends at $T_5$). Consequently, according to the present invention, the expiration stage (phases III and IV) is shortened relative to the natural, uncorrected, expiration cycle, in order to provide the corrective treatment.

If the pharyngeal conduit 110 were allowed to collapse totally or substantially, then it would require air at higher pressure to cause it to open. However, if the pharyngeal conduit 110 were allowed to partially collapse, the pressure required to open it and to inflate it would be significantly less than that required under the total collapse. As a result, the timing of the excitation according to the present invention is important to reduce the magnitude or amplitude of the excitation.

To this end, the DPAP device 10 includes an excitation source 124 that is connected to a respiration sensor (or monitor) 126 via cables or fluid conduits 128 (that conduct a fluid or a gas). The respiration sensor 126 is provided with electrodes 127 that collect the desired respiration parameters, in order to allow the practitioner to personalize the optimal excitation point E for each individual.

One (or two) nasal tube (mask or wire) 130 is connected to the excitation source 124 at one end, with its other end partly inserted in (or covering) the nasal cavity 112. According to another preferred embodiment, an oral tube or an electrical wire 132, or a dental appliance 150, is connected to the excitation source 124 at one end, with its other end partly inserted in (or covering) the mouth 134. According to still another embodiment, both the nasal tube 130 and oral tube 132 are connected to the excitation source 124, by means of a valve 136.

Considering now the respiration sensor/monitor 126, its main functions are: (1) upon initialization of the DPAP device 10 for the first time, the respiration sensor/monitor 126 assists the practitioner to determine the optimal excitation point E for the particular use of the DPAP device 10; and (2) for the normal use of the device, the respiration sensor/monitor 126 confirms the occurrence or presence of the excitation point E, and upon such confirmation it provides the necessary excitation to the user of the DPAP device 10.

The respiration sensor/monitor 126 uses the electrodes 127 [27] to monitor the respiratory cycle 200, and the progress of its four phases (I, II, III, IV), as is known or available in the field. As an example, the respiration sensor/monitor 126 monitors the variations in the relative position of the chest (as is currently done in a sleep study) in order to calculate the occurrence of the parameters of the excitation point E: the dilation $D_0$ and the excitation period $E_0$: $E(D_0, E_0)$.

According to another embodiment of the present invention, the respiration sensor/monitor 126 provides a feedback as to the efficacy of the excitation provided by the DPAP device 10 so as to vary the dilation $D_0$ and the excitation period $E_0$: $E(D_0, E_0)$ of the excitation point E.

As an example, under certain conditions, such as when the individual or user is sick and his/her respiration cycle does not follow the normal respiratory cycle. As an illustration, if the respiration sensor/monitor 126 determines the virtual time $T_4$, when the upper airway (102) dilator muscles are expected to be least active, and the positive intraluminal pressure is the lowest (from previous measurements during respiratory cycles), and further determines that this virtual time $T_4$ is different from the usual or normal virtual time $T_4$ that was determined at the initialization stage, then the respiration sensor/monitor 126 could automatically adjust the dilation parameter $D_0$ of the pharyngeal conduit 110 accordingly.

As another illustration, the respiration sensor/monitor 126 determines variations from the norm of the dilation parameter $D_0$ of the pharyngeal conduit 110, then it could automatically adjust the virtual time $T_4$, could accordingly. In a preferred embodiment, the dilation $D_0$ exceeds approximately 1 mm and the excitation period $E_0$ exceeds approximately 1 millisecond.

Considering now the excitation source 124 could provide a variety of excitations, some of which are: a puff of positive air pressure, oxygen, another gas, electrical, and/or an audible (or sound) vibratory wave. To this end, in order for the excitation source 124 to provide a short puff of air or gas (i.e., oxygen or another gas), the excitation source 124 includes a pump similar to that used in the CPAP device.

One distinction between the common CPAP device and the DPAP device 10 of the present invention is that in the present DPAP device 10 the puff of positive air is discontinuous, that is a puff of air is delivered at the desired pressure but only for a very short period of time, such as 0.5 second. Another desirable feature of the present DPAP device 10 is that the air puff pressure that this delivered intermittently (or periodically) could be lower than the pressure at which air is continuously delivered by the CPAP device, in that the air puff is delivered at the optimal excitation point E, prior to the collapse of the pharyngeal conduit 110.

According to another embodiment, in order for the excitation source 124 to provide an electrical excitation, the excitation source 124 includes an electrical stimulation device, such as those used, for example, in cardiac pacemakers or tachycardiac devices.

According to still another embodiment, in order for the excitation source 124 to provide an audible (or sound) vibratory wave, the excitation source 124 includes a sound pressure pump capable of generating vibratory waves, such as sound waves or other audible waves that are not limited to the audible frequency spectrum. The vibratory frequencies of the waves are selected to selectively cause selected elements, muscles, ligaments, cartilage, or cavities to vibrate or resonate.

For example, the excitation source delivers a wave at, or about, the resonance or vibration frequency of the nasal cavity 112, at the excitation point E. According to still other embodiments, the excitation source 124 delivers a wave at, or about, the resonance or vibration of the pharyngeal conduit 110, the tongue 114, the palate 119, the epiglottis, the uvula 120, the salivary glands, the larynx/trachea 106, the esophagus 108, and/or other muscles or cartilages, including the hyoid bone 118, that can cause the premature reversal of the respiratory cycle 200, as described earlier.

In a specific preferred embodiment where the dental appliance 150 is used in conjunction with the oral tube 132 for delivering the puff of gas, the dental appliance 150 may be made of the same material as the oral tube 132 for allowing the gas to pass therethrough. It includes a formable or compliant section 152 that fits over the user's teeth or gum 160, and an internal extension 154 secures the dental appliance 150 to the teeth or gum 160. An oral extension extends from, and is in fluidic communication with the oral tube 132 via the compliant section 152, into the user's mouth 134.

Figure 3:
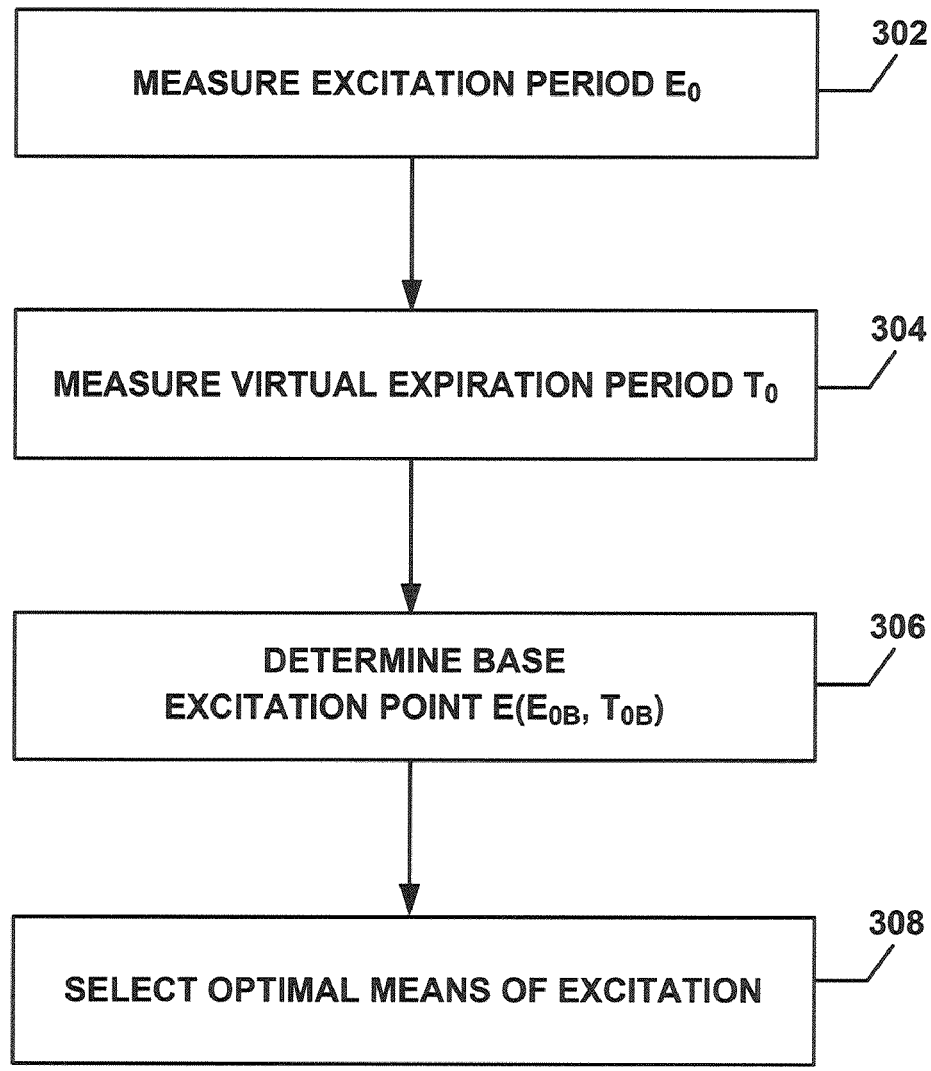
Figure 4:
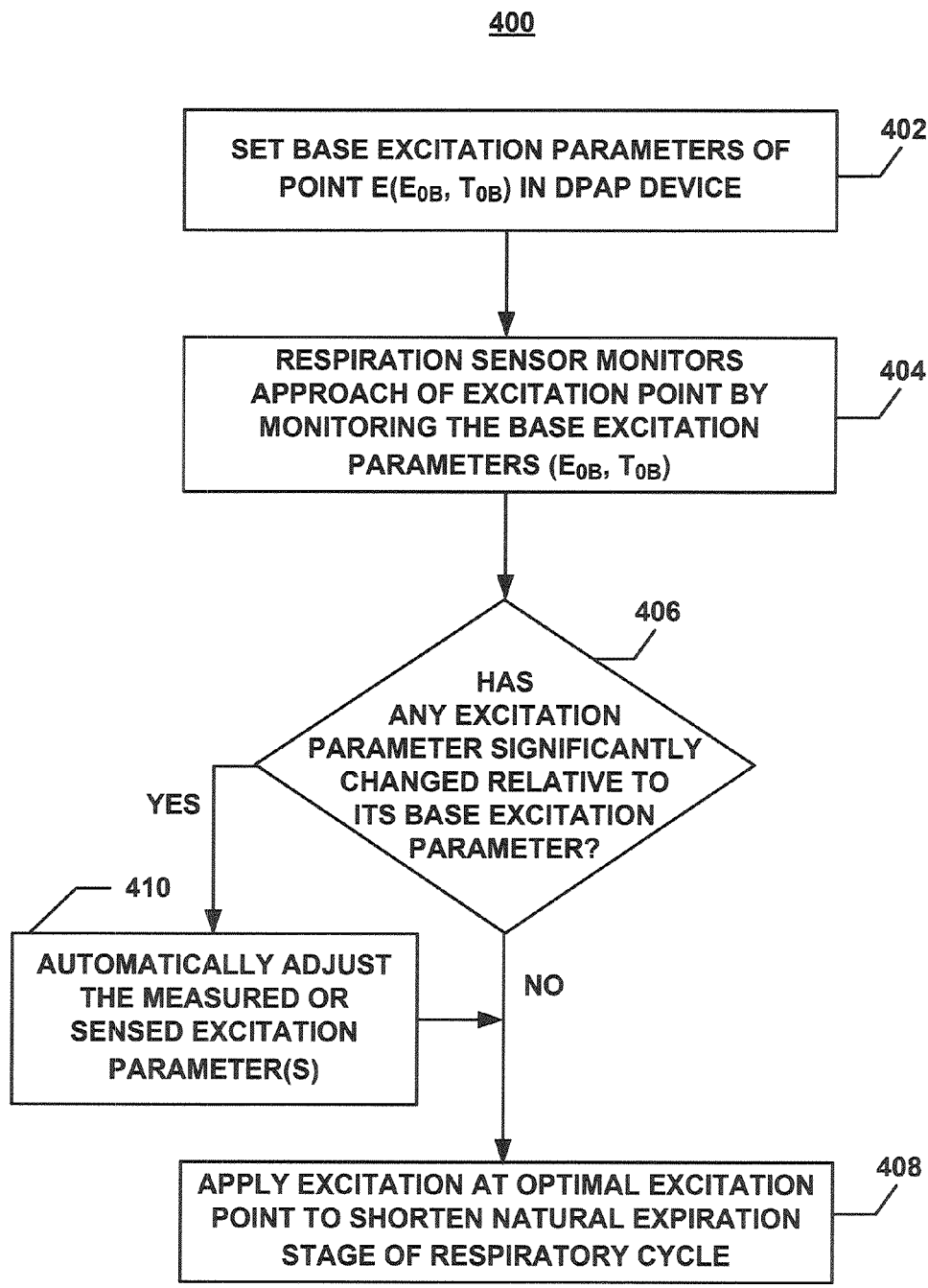

FIGS. 3 and 4 are flow charts illustrating the process of using the DPAP device 10 of FIG. 1 for reducing sleep disordered breathing events, as shown in the chart of FIG. 2. More specifically, FIG. 3 illustrates a method 300 for initializing the DPAP device of FIGS. 1 and 2.

At step 302, method 300 measures the base excitation period $E_{OB}$, pursuant to the chart of the respiratory cycle 200 of FIG. 2. At step 304, method 300 measures the base virtual period $T_{4B}$. Based on these parameters of the base excitation period $E_{OB}$ and the base virtual period $T_{4B}$, method 300 determines the optimal excitation point E for the particular user.

Considering now FIG. 4, it illustrates the general steps of a method 400 using the DPAP device 10 of FIG. 1 that has been initialized according to method 300 of the present invention. At step 402, method 400 sets the base excitation parameters ($E_{OB}$, $T_{4B}$) of the excitation point E that were determined pursuant to method 300 of FIG. 3.

At step 404, the respiration sensor 126 (FIG. 1) monitors the approach of the excitation parameters ($E_0$, $T_4$) of the excitation point E to their respective base values ($E_{OB}$, $T_{4B}$). At step 406, as soon as the excitation parameters reach, or closely approach, their respective base values ($E_{OB}$, $T_{4B}$), method 400 inquires if any of the excitation parameters ($E_0$, $T_4$) of the excitation point E has significantly changed relative to its respective base value ($E_{OB}$, $T_{4B}$), i.e., within an acceptable range, for instance 1% to 15%.

If method 400 determines that any of the excitation parameters ($E_0$, $T_4$) of the excitation point E has not significantly changed relative to its respective base values ($E_{OB}$, $T_{4B}$), then method 400 proceeds to step 408. At step 408, method 400 applies the excitation at the excitation point E, in order to shorten the natural excitation stage.

If method 400 determines at step 406 that one or both of the excitation parameters ($E_0$, $T_4$) of the excitation point E has significantly changed relative to its respective base values ($E_{OB}$, $T_{4B}$), then method 400 proceeds to step 410. At step 410, method 400 automatically adjusts the unchanged parameter and thus adjusts the occurrence of the excitation point E.

Method 400 then proceeds to step 408 and applies the excitation at the excitation point E, in order to shorten the natural excitation stage.

It is to be understood that the specific embodiments of the invention that have been described are merely illustrative of certain application of the principle of the present invention. Numerous modifications may be made to the description herein, without departing from the spirit and scope of the present invention.

What is claimed is:

1. A discontinuous positive airway pressure (DPAP) device for use by an individual, to reduce disordered breathing events, the DPAP device comprising:
    a sensor for determining an excitation point, E, that precedes a virtual natural expiration point, $T_4$, for a respiration cycle of the individual, by a virtual excitation period, $E_0$;
    wherein the excitation point, E, is selected during an exhalation period of the respiration cycle;
    wherein the excitation period, $E_0$, does not exceed the exhalation period;
    an excitation source responsive to the sensor, for discontinuously delivering an excitation, during a part of the excitation period, $E_0$, to at least one element of a respiratory path of an upper airway of the individual, at the optimal excitation point, E.

2. The DPAP device of claim 1, wherein the excitation causes a premature termination of a current exhalation stage.

3. The DPAP device of claim 1, wherein said at least one element of the respiratory path of the upper airway includes any one or more of: a pharyngeal conduit, a pharyngeal muscle, a pharyngeal cartilage, and a biological part along the respiratory path of the upper airway of the individual.

4. The DPAP device of claim 3, wherein the excitation source is connected to the respiration sensor via any one or more of: a cable and a fluid conduit.

5. The DPAP device of claim 4, wherein the excitation source further includes at least one electrode that collects respiration parameters, in order to allow the personalization of the optimal excitation point, E, of the individual.

6. The DPAP device of claim 1, further comprising any one or more of: a nasal tube, a mask, a wire, and a dental appliance, that is connected to the excitation source.

7. The DPAP device of claim 1, wherein the excitation source selectively applies the excitation to any one or more of: the individual's mouth to induce a salivation cycle, the individual's nasal cavity, and any one or more of the individual's at least one element of the respiratory path of the upper airway.

8. The DPAP device of claim 7, wherein the excitation source selectively selects between two or more different modes of excitation.

9. The DPAP device of claim 8, wherein the two or more different modes of excitation include any one or more of: a puff of positive gas pressure, an electrical excitation, an excitation at a sound frequency, and a vibratory wave.

10. The DPAP device of claim 1, wherein the excitation source delivers a vibratory wave at approximately a resonance frequency of said at least one element of the respiratory path of the upper airway.

11. The DPAP device of claim 1, wherein the respiration sensor provides a feedback to the excitation source regarding an efficacy of the excitation provided by the excitation source, so as to vary any one of a dilation of the respiratory path of the upper airway, $D_0$, and the excitation period, $E_0$.

12. A discontinuous positive airway pressure (DPAP) method for use by an individual, to reduce disordered breathing events, the DPAP method comprising:
    a sensor determines an excitation point, E, that precedes a virtual natural expiration point, $T_4$, for a respiration cycle of the individual, by a virtual excitation period;
    wherein the excitation point, E, is selected during an exhalation period of the respiration cycle;
    wherein the excitation period, $E_0$, does not exceed the exhalation period, $E_0$;
    an excitation source responsive to the sensor, discontinuously delivers an excitation, during a part of the excitation period, $E_0$, to at least one element of a respiratory path of an upper airway of the individual, at the optimal excitation point, E.

13. The DPAP method of claim 12, wherein selectively exciting the at least one element of the respiratory path of an upper airway further comprises selecting a target dilation of the respiratory path of an upper airway for the application of the excitation to said at least one element of the respiratory path of an upper airway.

14. The DPAP method of claim 13, wherein the sensor determines if any one of the parameters varies, and if so, varying the other parameters.

15. The DPAP method of claim 12, wherein said at least one element of the respiratory path of an upper airway includes any one or more of: a pharyngeal conduit, a pharyngeal muscle, a pharyngeal cartilage, and an element along the respiratory path of the upper airway of the individual.

16. The DPAP method of claim 12, wherein the excitation causes a premature termination of a current exhalation stage.

17. The DPAP method of claim 12, wherein the excitation enables a premature reversal of the respiratory cycle.

18. The DPAP method of claim 12, wherein the excitation prevents a total collapse of the respiratory path of the upper airway.

19. The DPAP method of claim 12, wherein the sensor determines the excitation point, E, as a function of the following parameters: a dilation $D_0$ of the upper airway, the excitation period $E_0$, and an amplitude of the excitation.

20. The DPAP method of claim 12, wherein the respiratory path of the upper airway of the individual includes any one or more of: a tongue, a palate, an epiglottis, an uvula, a salivary gland, a larynx/trachea, an esophagus, and a hyoid bone.

* * * * *